United States Patent
Ikehara et al.

(10) Patent No.: US 8,070,690 B2
(45) Date of Patent: Dec. 6, 2011

(54) BONE MARROW HARVESTING DRILL

(75) Inventors: Susumu Ikehara, Moriguchi (JP); Hiroshi Shirafuji, Takasaki (JP); Shuji Nakamura, Takasaki (JP); Nobuo Shimoda, Takasaki (JP); Katsuyuki Sado, Takasaki (JP)

(73) Assignees: Jimro Co., Ltd., Gunma (JP); Kansai Medical University, Osaka (JP)

( * ) Notice: Subject to any disclaimer, the term of this patent is extended or adjusted under 35 U.S.C. 154(b) by 375 days.

(21) Appl. No.: 12/018,337

(22) Filed: Jan. 23, 2008

(65) Prior Publication Data

US 2008/0177200 A1 Jul. 24, 2008

(30) Foreign Application Priority Data

Jan. 23, 2007 (JP) .................. 2007-012791

(51) Int. Cl.
*A61B 10/02* (2006.01)
(52) U.S. Cl. ................................... 600/567
(58) Field of Classification Search .............. 600/562, 600/563, 564, 567, 568
See application file for complete search history.

(56) References Cited

U.S. PATENT DOCUMENTS

| | | | | |
|---|---|---|---|---|
| 4,543,966 A | * | 10/1985 | Islam et al. | 600/567 |
| 5,012,818 A | * | 5/1991 | Joishy | 600/567 |
| 5,477,862 A | * | 12/1995 | Haaga | 600/567 |
| 5,758,655 A | * | 6/1998 | Como Rodriguez et al. | 600/562 |
| 7,077,845 B2 | * | 7/2006 | Hacker et al. | 606/80 |
| 2002/0042581 A1 | * | 4/2002 | Cervi | 600/567 |
| 2003/0233114 A1 | * | 12/2003 | Merboth et al. | 606/185 |
| 2003/0236506 A1 | * | 12/2003 | Schofield et al. | 604/272 |
| 2004/0077973 A1 | * | 4/2004 | Groenke et al. | 600/567 |
| 2004/0215102 A1 | | 10/2004 | Ikehara et al. | |
| 2006/0184174 A1 | | 8/2006 | Harris, Jr. et al. | |
| 2006/0247552 A1 | * | 11/2006 | Ikehara et al. | 600/562 |
| 2006/0247653 A1 | | 11/2006 | Akerfeldt et al. | |
| 2007/0016100 A1 | * | 1/2007 | Miller | 600/567 |
| 2007/0149980 A1 | * | 6/2007 | Seedhom et al. | 606/99 |

FOREIGN PATENT DOCUMENTS

| | | |
|---|---|---|
| JP | 2003/024339 A | 1/2003 |
| WO | 03/015637 A1 | 2/2003 |
| WO | 03/101307 A1 | 12/2003 |

OTHER PUBLICATIONS

An ended European Search Report dated Jun. 5, 2008.

* cited by examiner

*Primary Examiner* — Max Hindenburg
*Assistant Examiner* — Michael C Stout
(74) *Attorney, Agent, or Firm* — Sughrue Mion, PLLC

(57) ABSTRACT

The bone marrow harvesting drill of the invention includes an inner needle having a cutting edge at the tip thereof; a tubular mantle that receives the inner needle thereinto so that the inner needle and the tubular mantle are detachably attached; and a lock mechanism that prevents the axial rotation of the tubular mantle and the inner needle relative to each other; the inner needle having a groove formed at the tip thereof projecting from the tubular mantle for discharging bone scraps produced by the cutting edge at the tip of the inner needle; and the tubular mantle having a cutting edge formed at the tip edge thereof and a helical groove extending from the tip edge to at least part of the peripheral surface of the tubular mantle so as to be flush with the groove of the inner needle.

8 Claims, 12 Drawing Sheets

BONE MARROW HARVESTING DRILL

TECHNICAL FIELD

The present invention relates to a bone marrow harvesting drill to be used for, for example, drilling a bone to harvest bone marrow.

BACKGROUND ART

Bone marrow has generally been harvested using a bone marrow puncture needle to manually puncture the ilium. This kind of bone marrow puncture needle is constructed in such a manner as to insert and fit an inner needle into a tubular mantle while allowing the tip of the inner needle to project from the mantle. The bone marrow puncture needle, which is equipped with a handle in the mantle, percutaneously punctures the ilium, and once the tip of the needle reaches bone marrow, the inner needle alone is drawn out and the mantle remains in contact with the bone marrow for subsequent use.

As a method for harvesting bone marrow using this bone marrow puncture needle, typically, an aspiration method is employed. The aspiration method is such that the mantle of the bone marrow puncture needle is connected to a syringe to collect bone marrow by virtue of the aspiration force. In this method, however, since the quantity of bone marrow harvested from one site of a bone is as small as several ml, collecting a sufficient quantity of bone marrow requires a number of sites to be punctured. Further, a large amount of peripheral blood is allowed to mix into the harvested bone marrow. Consequently, the method, when used in allogeneic bone marrow transplantation, carries a high risk of causing GVHD (Graft versus Host Disease), which necessitates immunosuppression.

Under these circumstances, a bone marrow perfusion method has been developed as a method for overcoming the above problems. In the bone marrow perfusion method, two bone marrow harvesting needles are placed in contact with bone marrow so as to slowly perfuse bone marrow with a perfusion medium such as sterilized physiological saline. One of the needles is connected to a bone marrow harvesting set, and a bone marrow harvesting bag of the set is connected to an injection syringe or a tube of a parenteral fluid pump to aspirate bone marrow. Using a syringe that is filled with a perfusion medium and is connected to the other needle, the perfusion medium is injected slowly into the bone marrow in such a manner as to wash away the bone marrow, and thereby a required quantity of the bone marrow is harvested into the harvesting set in a short time. The bone marrow harvested in this way can be used not only for bone marrow transplantation but also for regenerative medicine.

However, the bone marrow puncture needle that is conventionally employed, which is constructed to be inserted into a bone manually by holding a handle, is not suitable for application to the bone marrow perfusion method from the viewpoint of the puncture rate and other factors.

Thus, a method has been desired that drills and punctures a bone in a short time using a bone marrow harvesting needle equipped with an electric drill that is capable of providing powerful rotational power. For this reason, a bone marrow harvesting needle has been proposed that includes an inner needle with a drilling edge; and a mantle with an angled edge formed at its tip, the mantle being allowed to rotate at a reduced speed with respect to the rotation of the inner needle through a speed reduction mechanism (WO 03/015637). This bone marrow harvesting needle makes it possible to reach the cavity accommodating the bone marrow in a significantly shorter time, and is also excellent in that bone scraps are discharged to the mantle, not into the body, because the bone scraps produced by the angled edge at the tip of the mantle are discharged upward in the mantle along a groove of the drill part of the inner needle. However, the viscosity of collagen, etc., contained in bone tissue resists the discharge of the bone scraps, thus limiting the reduction in the drilling time.

DISCLOSURE OF THE INVENTION

The present invention has been made in light of the above-described problems. Accordingly, a primary object of the invention is to provide a bone marrow harvesting drill capable of harvesting bone marrow more quickly from a donor by using a bone marrow perfusion method.

In order to accomplish the above object, the bone marrow harvesting drill of the invention comprises an inner needle having a cutting edge and a shank at the tip and the rear end thereof, respectively; a tubular mantle that receives the inner needle thereinto so that the inner needle and the tubular mantle are detachably attached in such a manner that the tip and the rear end of the inner needle project from the tubular mantle; and a lock mechanism that prevents the axial rotation of the tubular mantle and the inner needle relative to each other; the inner needle having a groove formed at the tip thereof projecting from the tubular mantle for discharging bone scraps produced by the cutting edge at the tip of the inner needle; and the tubular mantle having a cutting edge formed at the tip edge thereof and a helical groove extending from the tip edge of the tubular mantle to at least part of the peripheral surface of the tubular mantle so as to be flush with the groove of the inner needle.

Preferably, the cutting edge of the tubular mantle is formed in such a way that it is flush with the cutting edge of the inner needle.

Preferably, a flank formed at the tip edge of the tubular mantle is formed so as to be flush with a flank formed at the tip of the inner needle.

Preferably, the tubular mantle has a lure lock connector formed at the rear end thereof.

Preferably, the bone marrow harvesting drill further comprises a cap attached to the inner needle for sealing the lure lock connector that is formed at the rear end of the tubular mantle.

Preferably, the lock mechanism includes a locking part formed on the cap and a lock-receiving part formed in the tubular mantle for engaging with the locking part. The lock mechanism is structured so that the engagement of the locking part with the lock-receiving part prevents the axial rotation of the inner needle relative to the tubular mantle.

EFFECT OF THE INVENTION

According to the bone marrow harvesting drill of the invention, a bone is cut with the cutting edge formed at the tip of the inner needle and the cutting edge formed at the tip edge of the tubular mantle. Bone scraps produced by the cutting edge at the tip of the inner needle are discharged from the groove at the tip of the inner needle into the helical groove formed on the peripheral surface of the tubular mantle. Bone scraps produced by the cutting edge of the tubular mantle are also discharged from the helical groove. Thus, the drill of the present invention reduces the cutting resistance due to the clogging of the helical groove by bone scraps, thereby enabling the quick harvest of bone marrow.

BEST MODE FOR CARRYING OUT THE INVENTION

Preferable embodiments of the bone marrow harvesting drill according to the invention will be described below with reference to FIGS. 1 to 15.

Figure 1:
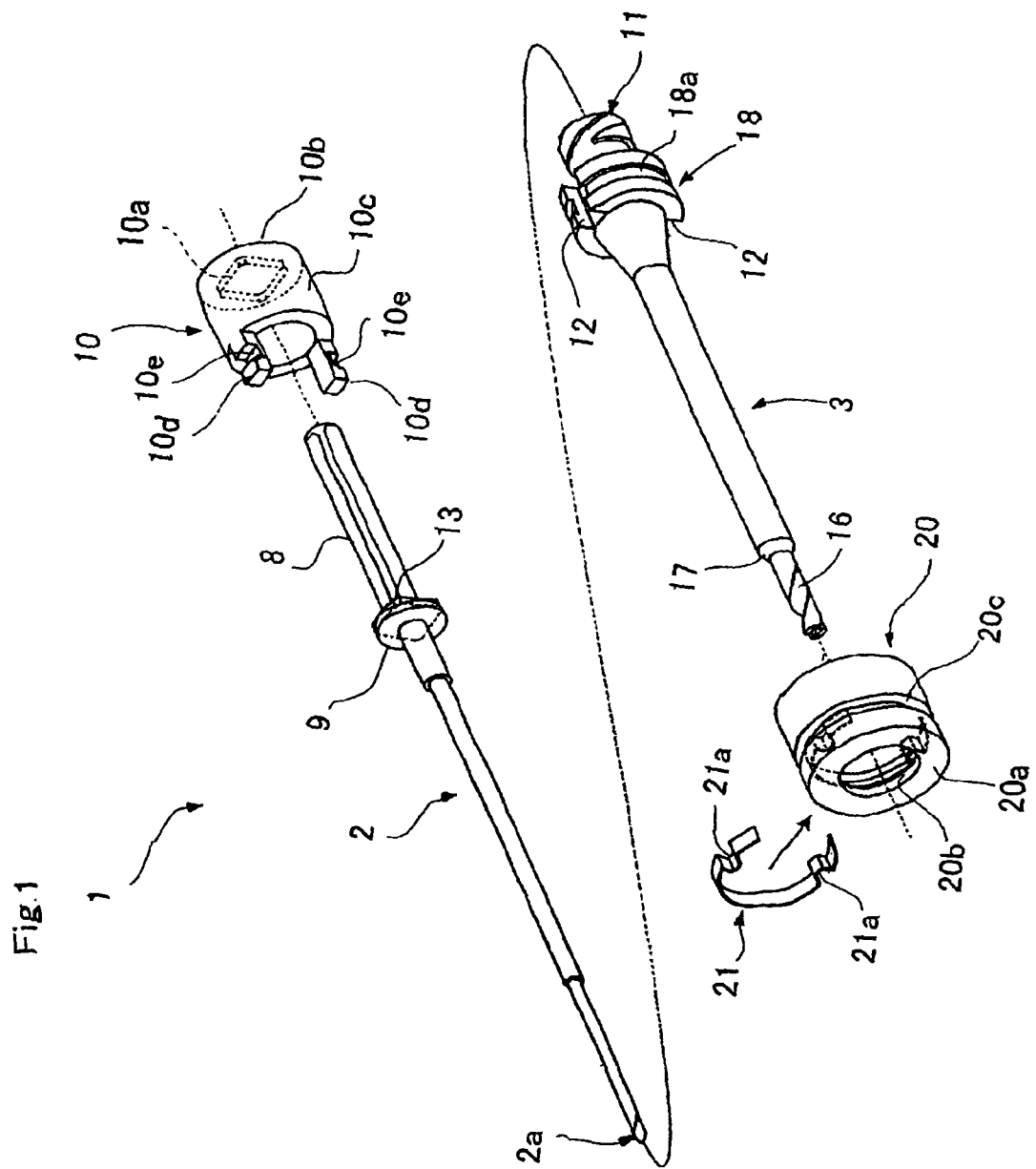
FIG. 1 is an exploded perspective view of a bone marrow harvesting drill in accordance with one embodiment of the invention.
Figure 2:
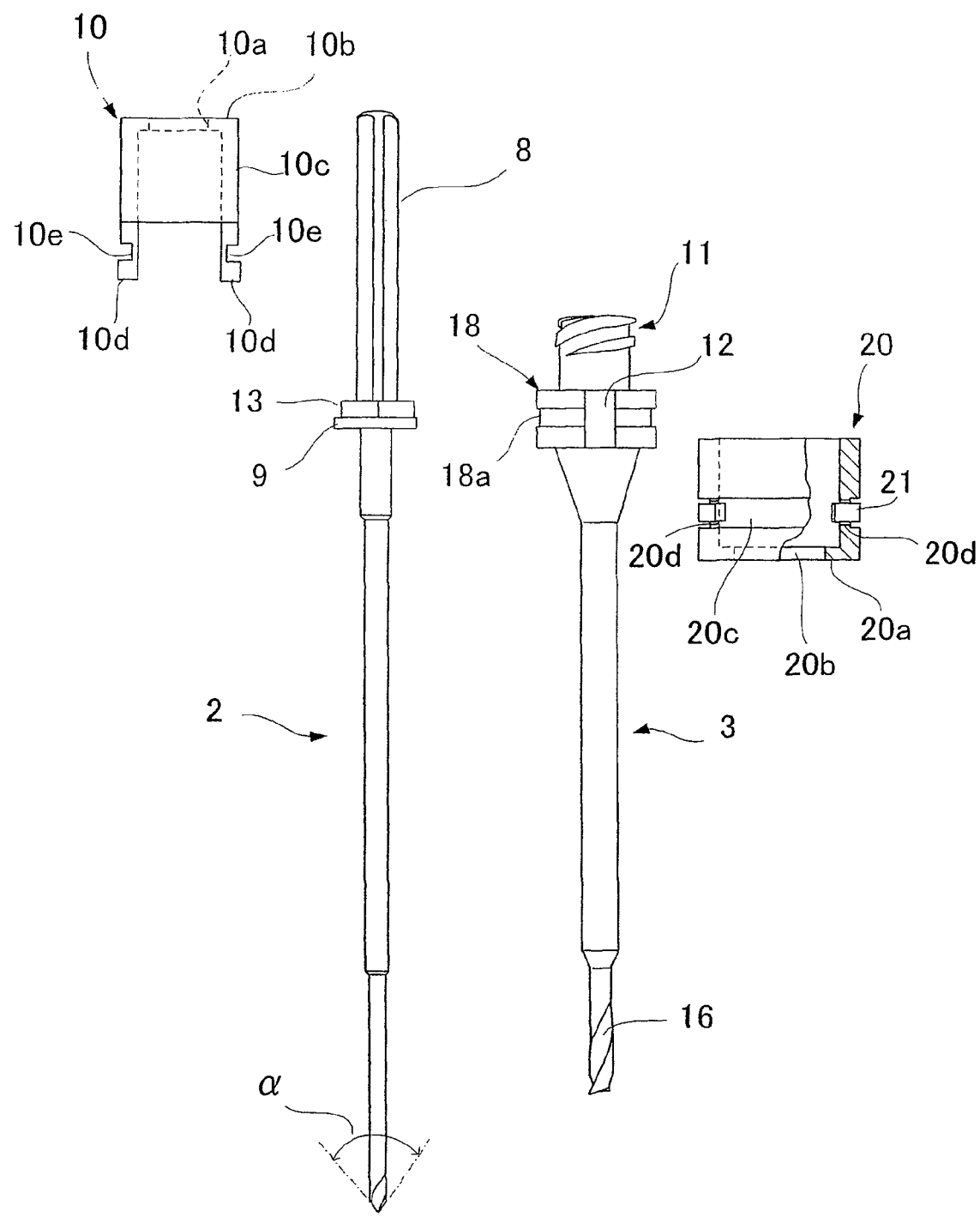
FIG. 2 is an exploded plan view of the bone marrow harvesting drill of FIG. 1.

FIG. 1 is an exploded perspective view showing a first embodiment of the bone marrow harvesting drill, and FIG. 2 is an exploded plan view. As shown in FIG. 1, a bone marrow harvesting drill 1 includes an inner needle 2 and a tubular mantle 3 into which the inner needle 2 can be inserted.

Figure 3:
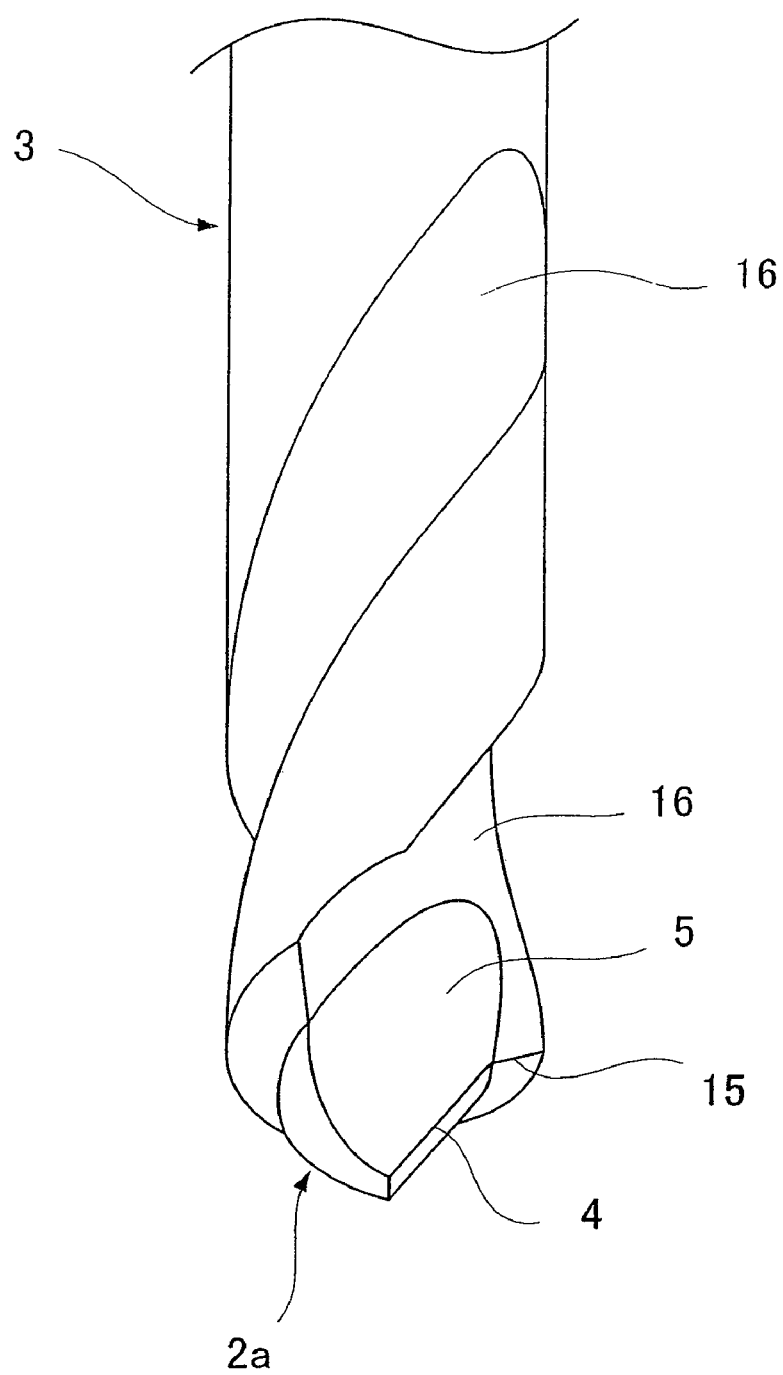
FIG. 3 is a plan view magnifying a part of the bone marrow harvesting drill of FIG. 1.
Figure 4:
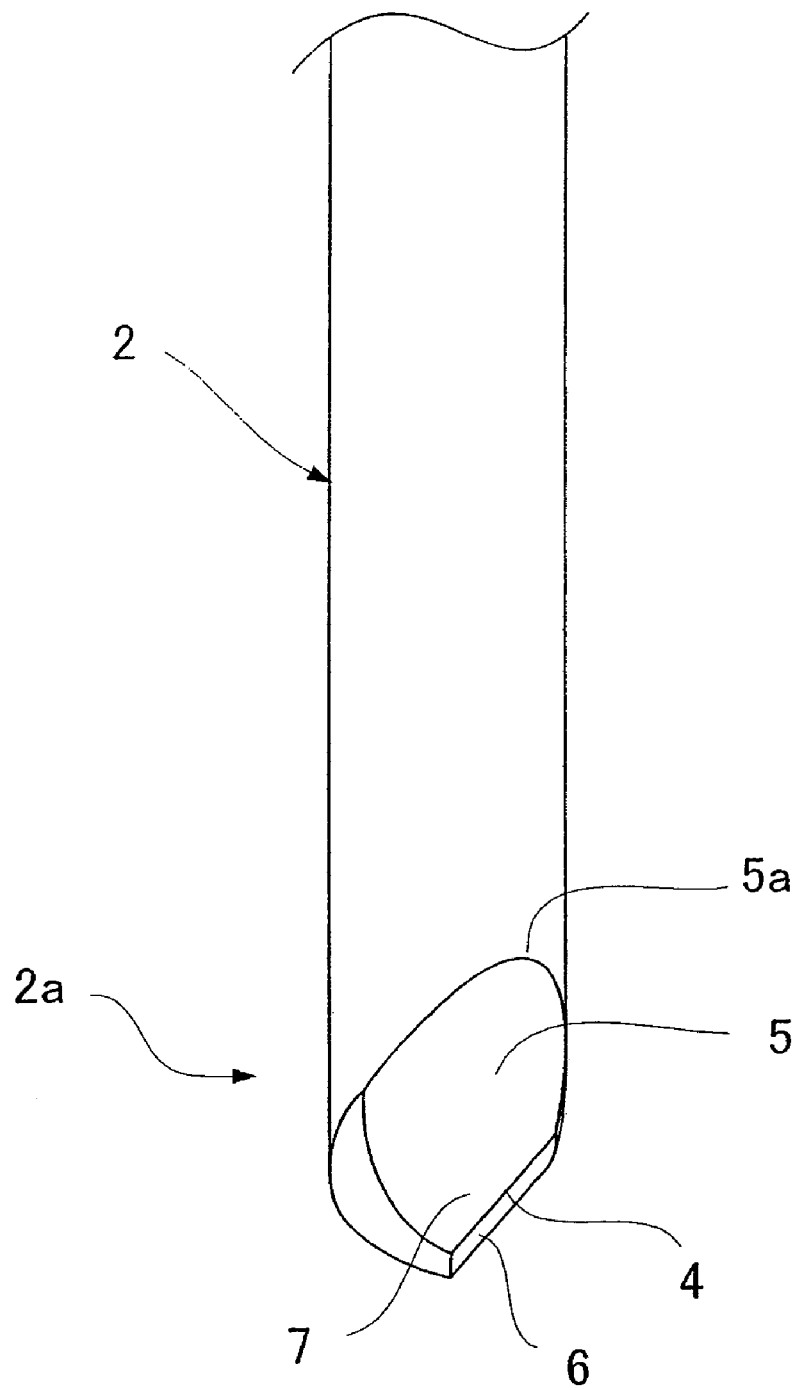
FIG. 4 is a plan view magnifying a part of the inner needle of the bone marrow harvesting drill of FIG. 1.

The inner needle 2 is, as enlarged in FIGS. 3 and 4, provided at its tip with a cutting edge 4 and a groove 5 for discharging bone scraps produced by the cutting edge 4. The cutting edge 4 is an intersection line of a flank 6 and a rake face 7. The tip 2a of the inner needle 2 preferably has a given tip angle α (FIG. 2).

The inner needle 2 is provided at its rear end with a shank 8 to be held in a drill chuck. The inner needle 2 is further provided with a circular flange 9 at the base of the shank 8. When the inner needle 2 is inserted into the tubular mantle 3, one side (the front face) of the flange 9 comes into contact with the rear end of the tubular mantle 3 at the position where the tip 2a of the inner needle 2 projects from the tubular mantle 3 as shown in FIG. 3, so that further insertion of the inner needle 2 into the tubular mantle 3 is not allowed.

The other side of the flange 9 provides a bearing surface, with which a lock cap 10 inserted from the back of the inner needle 2 can come into contact. The lock cap 10 has a bottom 10b provided with a hole 10a in the shape of a polygon (a quadrangle in the figure), a cylindrical part 10c, and a pair of locking parts 10d, 10d projecting from the end of the cylindrical part 10c. The lock cap 10 can accommodate a lure lock connector 11, which will be described later, of the tubular mantle 3. The locking parts 10d, 10d engage with lock-receiving parts 12, described later, of the tubular mantle 3.

On the other side (the back side) of the flange 9, a polygonal (quadrangular in the figure) plate 13 capable of fitting into the hole 10a of the lock cap 10 is fixed. Fitting the plate 13 into the hole 10a prevents the lock cap 10 from rotating relative to the inner needle 2 (see FIG. 6). The lock cap 10 may also be fixed to the inner needle 2 by welding, pin joint, or like means.

Figure 5:
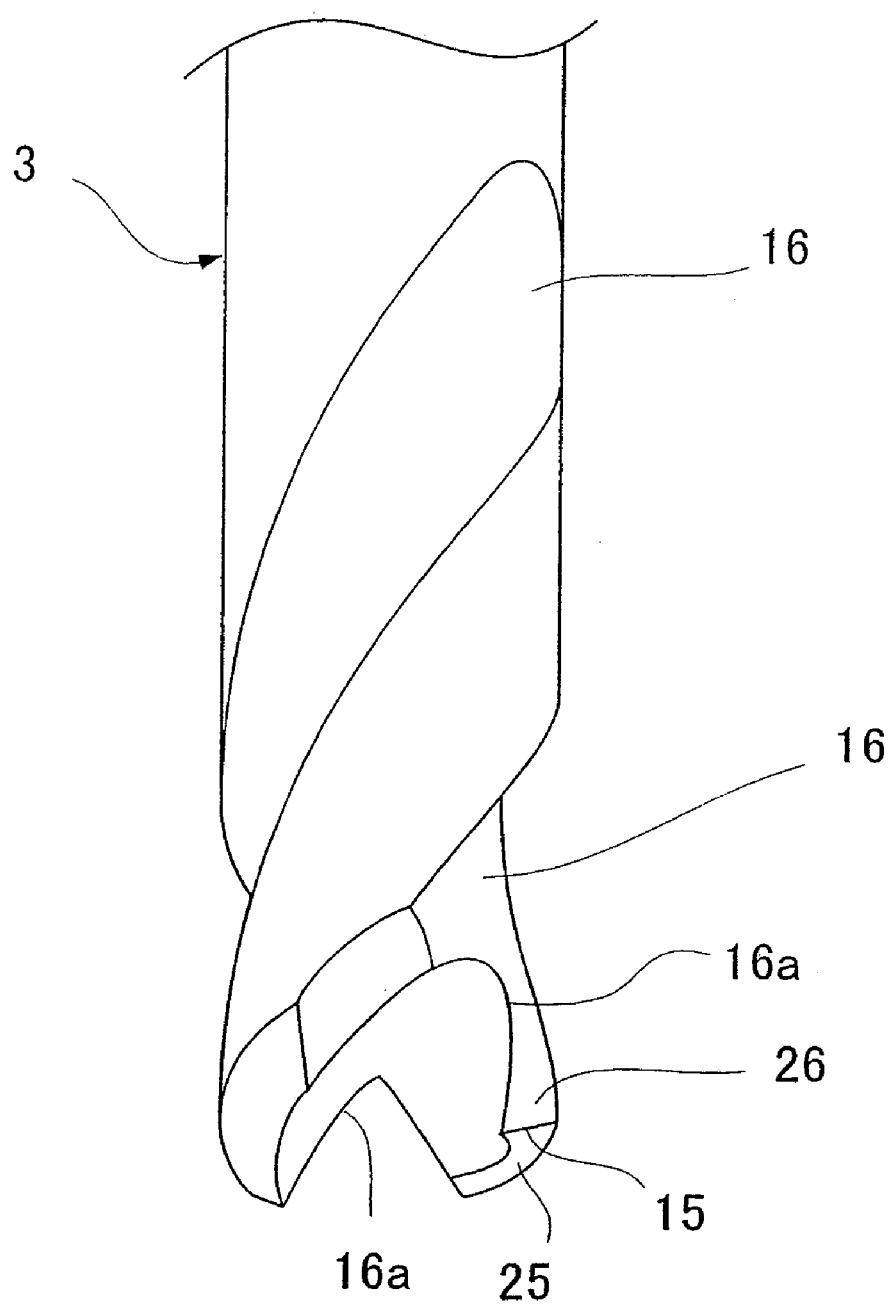
FIG. 5 is a plan view magnifying a part of the tubular mantle of the bone marrow harvesting drill of FIG. 1.
Figure 6:
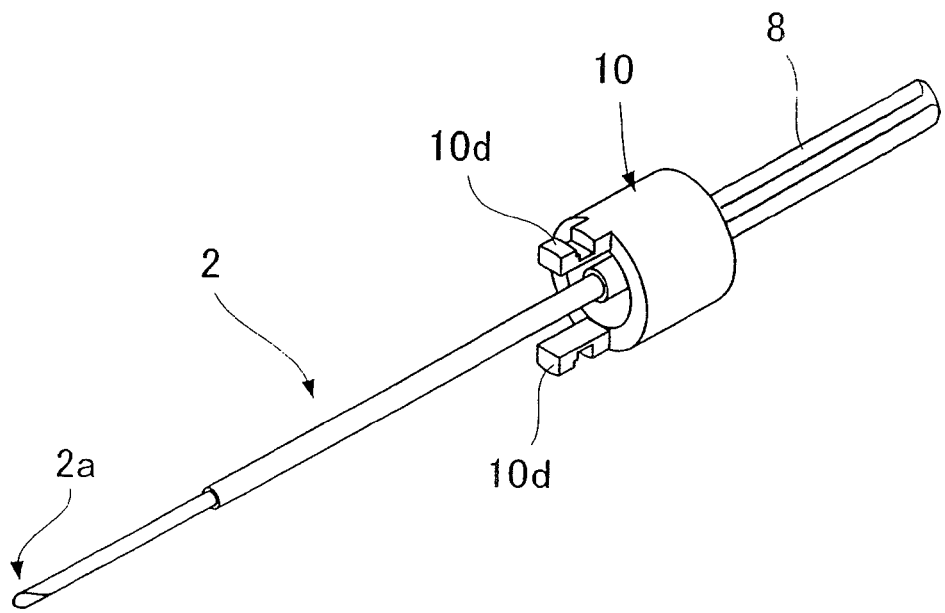
FIG. 6 is a perspective view of the inner needle of the bone marrow harvesting drill of FIG. 1, as equipped with a lock cap.

As enlarged in FIGS. 3 and 5, the tubular mantle 3 has a cutting edge 15 formed at the tip edge and a helical groove 16 extending from the tip edge to at least part of the peripheral surface of the tubular mantle 3.

The tubular mantle 3 preferably increases in diameter after the helical groove 16 via a stepped part 17 (FIG. 1) so as to regulate the drilling depth. A lure lock connector 11 is formed at the rear end of the tubular mantle 3.

The tubular mantle 3 further has a flange 18 formed at the base of the lure lock connector 11 so that the cylindrical part 10c of the lock cap 10 is seated on the flange 18. The flange 18 includes lock-receiving parts 12, as shown in FIGS. 1 and 2, that are constructed with a pair of grooves extending in the axial direction of the tubular mantle 3. The lock-receiving parts 12 is, as shown in FIG. 7, capable of receiving the projections that form the locking parts 10d of the lock cap 10, and engaging the same.

Figure 7:
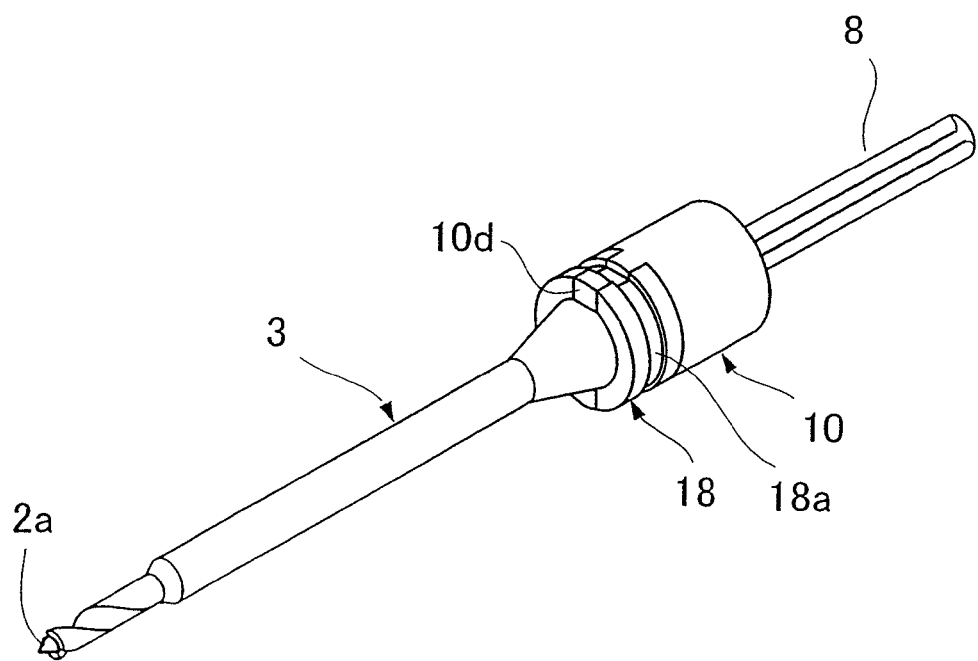
FIG. 7 is a perspective view of the inner needle and outer needle of the bone marrow harvesting drill of FIG. 1, as coupled so as not to rotate relative to each other.

As shown in FIG. 7, when the inner needle 2 is inserted into the tubular mantle 3 and the lock cap 10 is placed thereon, the lock cap 10 is seated on the flange 18 of the tubular mantle 3, thereby sealing the lure lock connector 11 formed in the tubular mantle 3. The engagement of the locking parts 10d with the lock-receiving parts 12 prevents the inner needle 2 and the tubular mantle 3 from axially rotating relative to each other, thus allowing them to rotate in an integrated manner.

In order to couple the lock cap 10 with the flange 18 of the tubular mantle 3, a coupling cap 20 may be used (FIGS. 1 and 2). The coupling cap 20 has a hole 20b defined by an inner flange 20a, and is constructed so that, when the tubular mantle 3 is inserted into the hole 20b, the coupling cap 20 covers the flange 18 of the tubular mantle 3, so that the inner flange 20a comes into contact with the flange 18. The coupling cap 20 has a concave groove 20c formed on its peripheral surface. The concave groove 20c is provided with a pair of holes 20d, 20d (FIG. 2) opposed to each other. A clip 21 is fitted into the concave groove 20c as shown by a dashed line in FIG. 1, and locking projections 21a, 21a, which expand inward at both ends of the clip 21, are received in the holes 20d, 20d of the concave groove 20c to project into the inner surface of the coupling cap 20. These projecting parts are engaged with a peripheral groove 18a formed on the peripheral surface of the flange 18 of the tubular mantle 3. The projections constituting the locking parts 10d of the lock cap 10 are also provided with concave portions 10e. When the lock cap 10 is seated on the flange 18, these concave portions 10e align with the position of the peripheral groove 18a of the flange 18. Each concave portion is slightly deeper than the peripheral groove 18a. Therefore, in the state wherein the coupling cap 20 is fitted over the flange 18, and the clip 21 is placed thereon so that the locking projections 21a of the clip 21 are engaged in the peripheral groove 18a of the flange 18, when the coupling cap 20 is rotated around the axis, the locking projections 21a are fitted and engaged into the concave portions 10e that are a slightly deeper than the peripheral groove 18a. Accordingly, the tubular mantle 3 and the inner needle 2 are coupled in a state wherein, as shown in FIG. 3, the tip 2a of the inner needle 2 projects from the front end of the tubular mantle 3.

Figure 8:
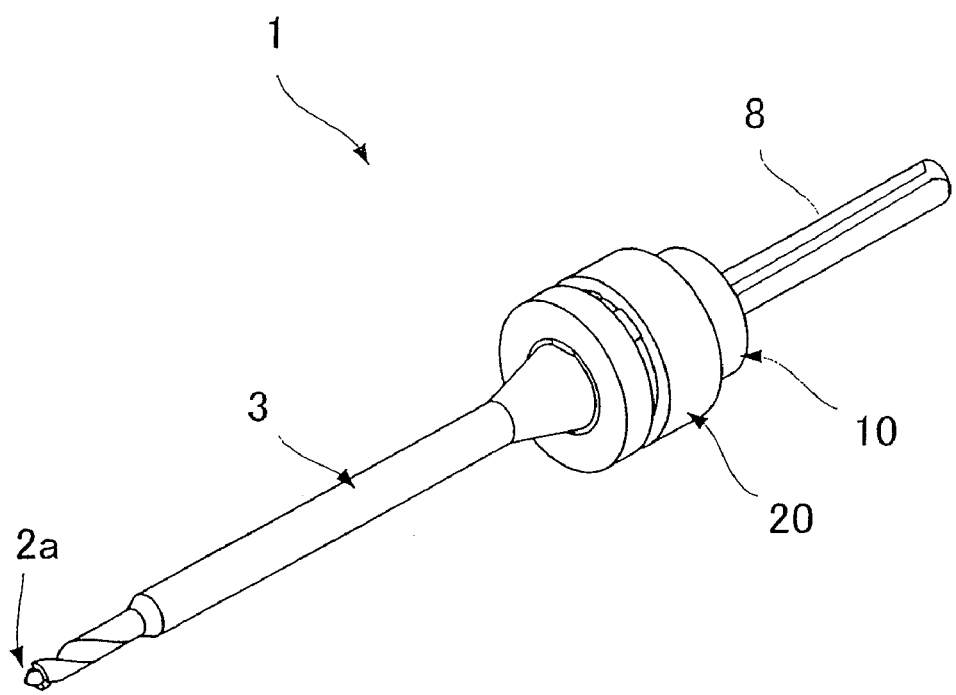
FIG. 8 is a perspective view of the bone marrow harvesting drill of FIG. 1 in the assembled state.

Thus, as shown in FIG. 8, the coupling cap couples the inner needle 2 with the tubular mantle 3 so that the inner needle 2 is not detached from the tubular mantle 3. In this state, they can be used as a drill.

The helical groove 16 of the thus-coupled tubular mantle 3 is formed so as to be flush with the groove 5 of the inner needle 2. This allows bone scraps that are produced by the cutting edge 4 of the inner needle 2 to be discharged from the groove 5 of the inner needle 2 through the helical groove 16 of the tubular mantle 3.

In order to discharge bone scraps from the groove 5 of the inner needle 2 through the helical groove 16, it is preferable, at the boundary between the groove 5 of the inner needle 2 and the helical groove 16, not to form a gap, step, pocket, or the like that can be clogged with the bone scraps. Such a structure prevents clogging by bone scraps, allowing the bone scraps to be smoothly discharged from the groove 5 to the helical groove 16. Further, because a gap between the cutting edge 4 of the inner needle 2 and the cutting edge 15 of the tubular mantle 3 causes resistance in cutting, such a gap is preferably narrowed as much as possible, thereby increasing the cutting capability.

In order to make the helical groove 16 of the tubular mantle 3 flush with the groove 5 of the inner needle 2, the helical groove 16 preferably has, in the leading edge at the boundary with the groove 5 of the inner needle 2, a concave notch 16a formed in conformity with the outline 5a of the groove 5 (FIG. 4), which is defined by the intersection line of the groove 5 of the inner needle 2 and the peripheral surface of the inner needle 2, as shown in FIG. 5. Even if the outline of the groove 5 is not in conformity with the outline of the notch 16a, it is sufficient as long as the construction allows the bone scraps in the groove 5 to be discharged into the helical groove 16.

In order to smoothly discharge bone scraps from the groove 5 to the helical groove 16, the cutting edge 15, a flank 25, and a rake face 26 of the tubular mantle 3 are preferably formed so as to be flush with the cutting edge 4, the flank 6, and the rake face 7 of the inner needle 2, respectively.

In the embodiment shown in FIG. 3, the cutting edge 4 and the cutting edge 15 have a different angle; however, the cutting edge 15 and the flank 25 of the tubular mantle 3 each preferably have an angle that agrees with the tip angle α of the inner needle 2.

Figure 9:
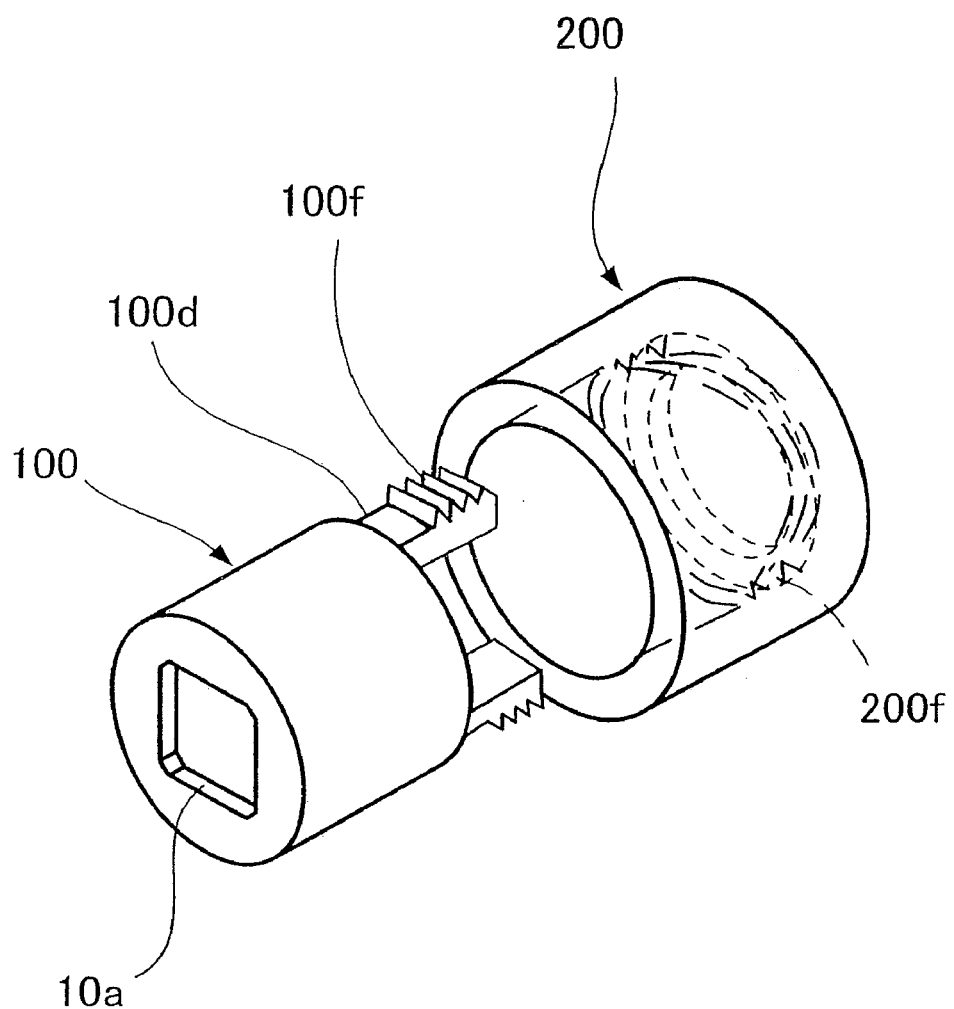
FIG. 9 is a perspective view of a lock cap and a coupling cap of the bone marrow harvesting drill in accordance with another embodiment.

The coupling of the inner needle 2 and the tubular mantle 3 is not limited to the above examples. For example, as shown in FIG. 9, it is also possible to form male screws 100f on the outer surface of the projections that constitute locking parts 100d of a lock cap 100, and female screws 200f on the inner surface of a coupling cap 200 to be screwed with the male screws 10f. Additionally, a structure, which is not illustrated, opposite to the illustrated example may be used. Specifically, the structure may be such that a flange provided with a groove that forms a lock-receiving part is formed on the tubular mantle, so that a lock cap provided with a projection that constitutes a locking part is installed thereon from the inner needle side, and a coupling cap is further installed thereon from the tubular mantle side, thereby giving a coupling.

Coupling of the tubular mantle 3 in a relatively unrotatable manner is thus achieved (FIG. 8). The shank 8 of such a bone marrow harvesting drill 4 is held in a drill chuck of a drill drive (not illustrated), and then the drill drive is driven to integrally rotate the inner needle 2 and the tubular mantle 3. An electric, air-driven, or like handheld drill drives may be suitably used as such a drill drive.

Next, an example of a bone marrow harvesting set for a bone marrow perfusion method using the bone marrow harvesting drill as above will be described.

The immunological functions of recipients, who are the subjects of bone marrow transplantation, organ transplantation, etc., are significantly lowered due to pretreatments such as X-ray irradiation. Therefore, reducing chances of subjects suffering from infectious diseases to a minimum is indispensable to treatments involving transplantation. In such a situation, the use of the below described bone marrow harvesting set for harvesting bone marrow by a bone marrow perfusion method can minimize the exposure of harvested bone marrow to a non-aseptic environment.

Figure 10:
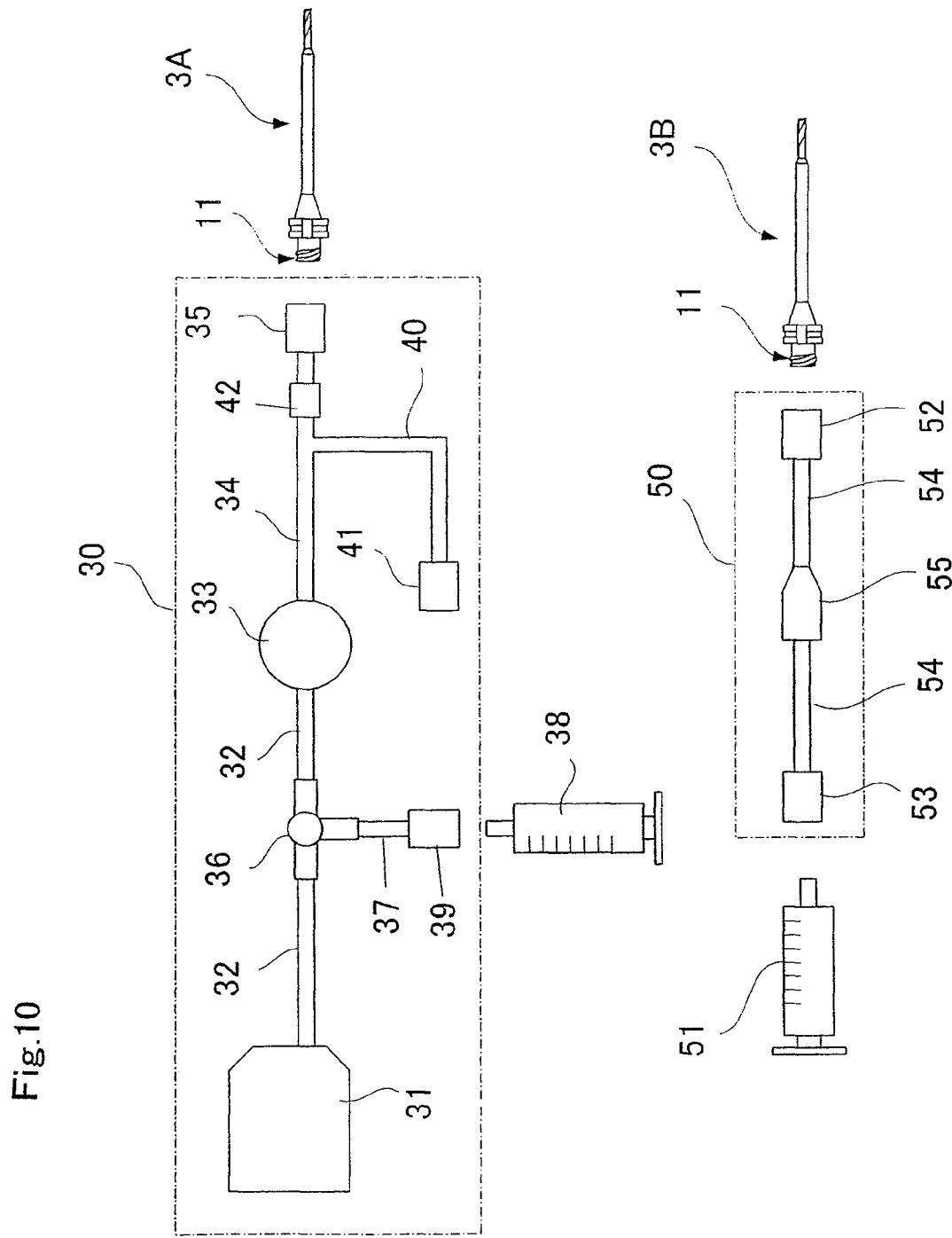
FIG. 10 is a plan view of a bone marrow harvesting set using the bone marrow harvesting drill of FIG. 1.

The bone marrow harvesting set for the bone marrow perfusion method includes, as shown in FIG. 10, a harvest circuit 30 for harvesting bone marrow and an injection circuit 50 for injecting a perfusion medium such as sterilized physiological saline.

According to one embodiment, the harvest circuit 30 includes, as shown in FIG. 10, a fluid collection container 31 for containing bone marrow harvested with physiological saline; a filter 33 connected to the fluid collection container 31 via a first tube 32 for filtering fatty tissues, etc.; a first lure lock connector 35 connected to the filter 33 via a second tube 34 and capable of fitting with a lure lock connector 11 of a tubular mantle 3A for harvesting bone marrow; a three-way stopcock 36 interposed in the first tube 32; and a second lure lock connector 39 connected to the three-way stopcock 36 via a third tube 37 for connecting an aspirating syringe 38. It is preferable that the second tube 34 be provided with a branch tube 40 for injecting heparinized saline solution, and that the branch tube 40 be provided with a third lure lock connector 41 so as to prevent blood coagulation. In the figure, the number 42 represents a one-way valve for preventing regurgitation to the bone marrow side.

The injection circuit 50 is, according to another embodiment, a tube that connects a syringe 51 for injecting a perfusion medium to a lure lock connector 11 of a tubular mantle 3B for injecting a perfusion medium. In the circuit 50, a fourth lure lock connector 52 to be connected to the lure lock connector 11 of the tubular mantle 3B is connected, via a tube 54, to a fifth lure lock connector 53 to be connected to the syringe 51, or to a parenteral fluid pump or a parenteral fluid bag hung at a height from a parenteral fluid stand, neither of which is illustrated. An air trap chamber 55 is interposed in the tube 54. Injection orifices of the syringes 38 and 51 to be connected with the harvest circuit 30 and the injection circuit 50, respectively, serve as lure lock connectors connectable with the lure lock connectors 39 and 53, respectively.

An example of harvesting bone marrow of the ilium using the above-described bone marrow harvesting drill and bone marrow harvesting set will be described with reference to FIGS. 11 to 15.

Figure 11:
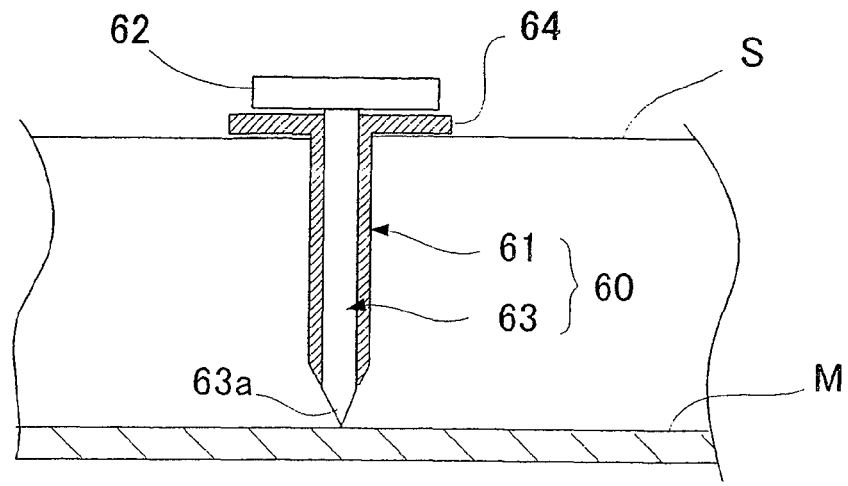
FIG. 11 is a diagram for explaining a method for harvesting bone marrow using the bone marrow harvesting drill of FIG. 1 and the bone marrow harvesting set of FIG. 10.

Bone marrow is harvested using a guide needle 60 as illustrated in FIG. 11. The guide needle 60 includes a guide cylinder 61 into which the bone marrow harvesting drill 1 can be fitted, and a shaft needle 63 provided with a head 62. The sharp tip 63a of the shaft needle 63 projects from the guide cylinder 61 when the shaft needle 63 is inserted into the guide cylinder 61. The upper end of the guide cylinder 61 is provided with an outer flange 64.

Figure 13:
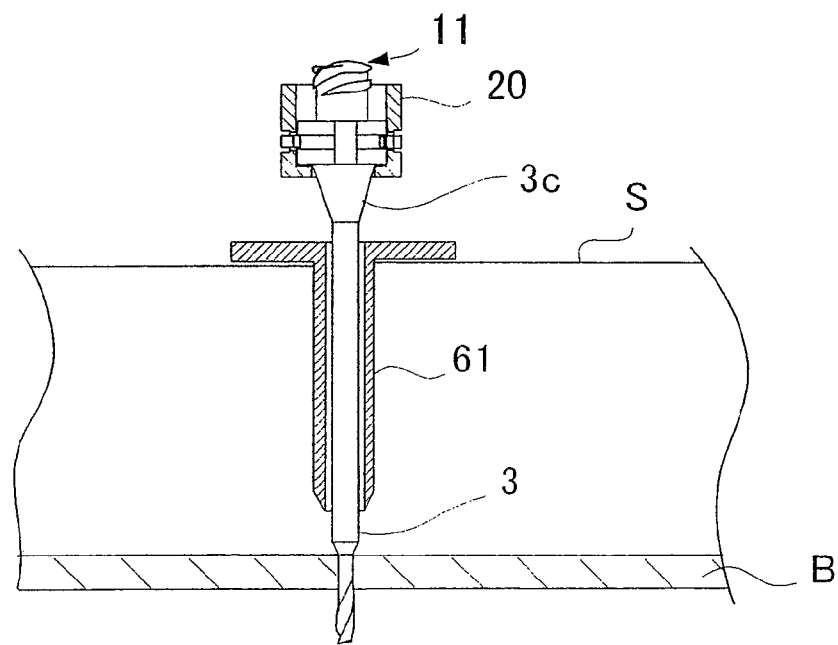
FIG. 13 is an explanatory diagram following FIG. 12 in sequence.
Figure 14:
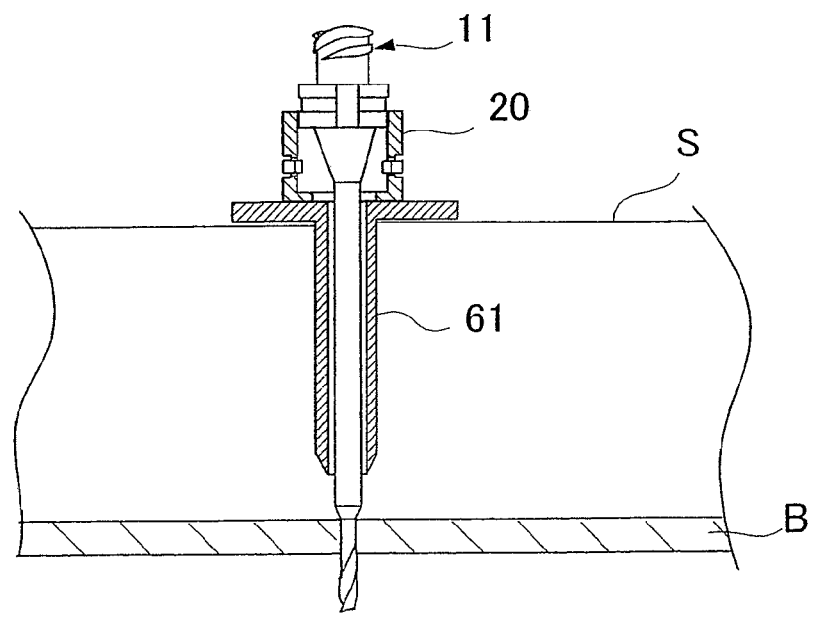
FIG. 14 is an explanatory diagram following FIG. 13 in sequence.

First, as shown in FIG. 11, skin S is incised with a scalpel, and the guide needle 60 is inserted into the skin from the incised site to allow the tip 63a of the shaft needle 63 of the guide needle 60 to reach a periosteum M. If the tip of the bone marrow harvesting drill 1 were inserted to reach the periosteum M without the guide needle 60, tissue would be greatly damaged by the cutting edges 4 and 15 of the inner needle 2 and the tubular mantle 3 of the bone marrow harvesting drill 1. The use of the guide needle can prevent such damage. The tubular mantle 3 is provided with a large-diameter part 3c in a tapered shape having a larger diameter than the inner diameter of the guide cylinder 61 (FIG. 13). This large-diameter part 3c serves as a stopper for the guide needle 60. The large-diameter part 3C limits the insertion depth of the tubular mantle 3, and, together with the stepped part 17 that limits the drilling depth, prevents accidents such as complete penetration.

If the positional relationship between the guide needle 60 and the bone is checked in advance by CT scan, etc., the site where the bone marrow harvesting needle 1 should be placed can be easily decided, and moreover, a record of such can be preserved.

Figure 12:
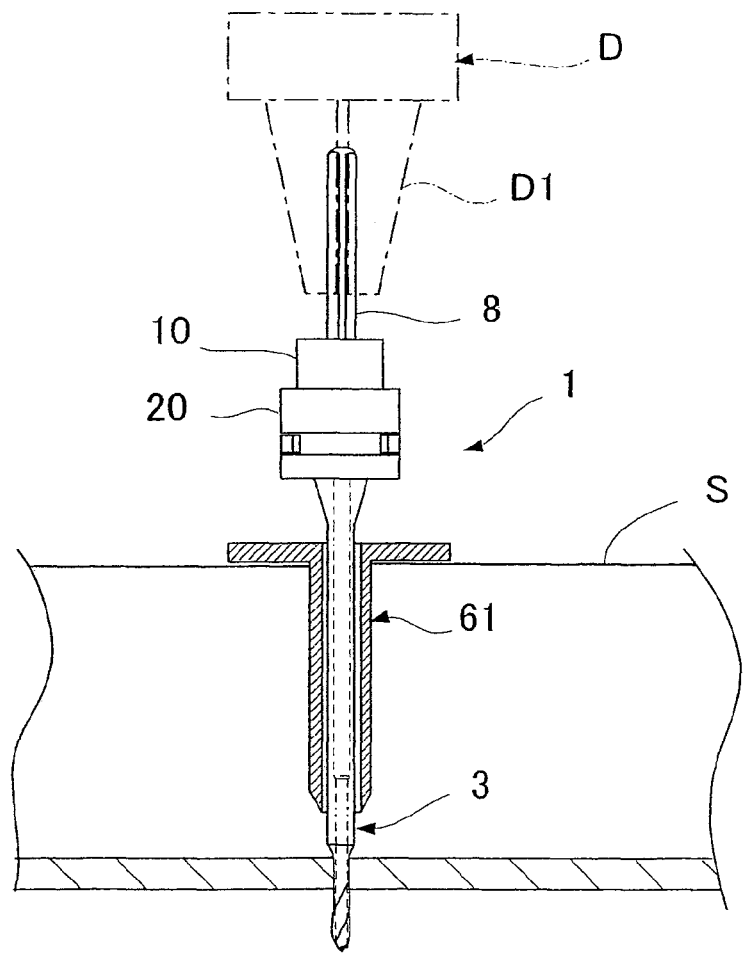
FIG. 12 is an explanatory diagram following FIG. 11 in sequence.

Next, as shown in FIG. 12, the shaft needle 63 of the guide needle 60 is drawn out from the guide cylinder 61, and the bone marrow harvesting drill 1 attached to an electric drill drive D (only the drill chuck is illustrated) is inserted into the retained guide cylinder 61. Then, the drill drive D is rotated while pressing the bone marrow harvesting needle 1 against the bone, so as to drill a hole in the bone.

After the tip of the bone marrow harvesting drill 1 reaches bone marrow, the coupling cap 20 of the bone marrow harvesting drill 1 is rotated to disengage the locking projections 21a from the concave portions 10e, allowing the inner needle 2 to be removed from the tubular mantle 3. Then, the drill drive D is lifted up while holding the shank 8 of the inner needle 2 in the drill chuck D1 of the drill drive D, and the inner needle 2 is drawn out from the tubular mantle 3.

When the inner needle 2 is drawn out from the tubular mantle 3, the lure lock connector 11 at the rear end of the tubular mantle, which is sealed with the lock cap 10 until then 10, appears, as shown in FIG. 13. In other words, the lure lock connector 11 can be protected from exposure to a non-aseptic environment until the inner needle 2 is drawn out from the tubular mantle 3. In the state as shown in FIG. 13, the coupling cap 20 is rotated to place the locking projections 21a into the grooves constituting the lock-receiving parts 12, whereby the coupling cap 20 is moved downward to leave the lure lock connector 11 fully exposed.

In this way, the tubular mantle 3 is placed in one end of the ilium B. Further, another tubular mantle 3 is placed in the other end of the ilium B in the same manner as above.

Figure 15:
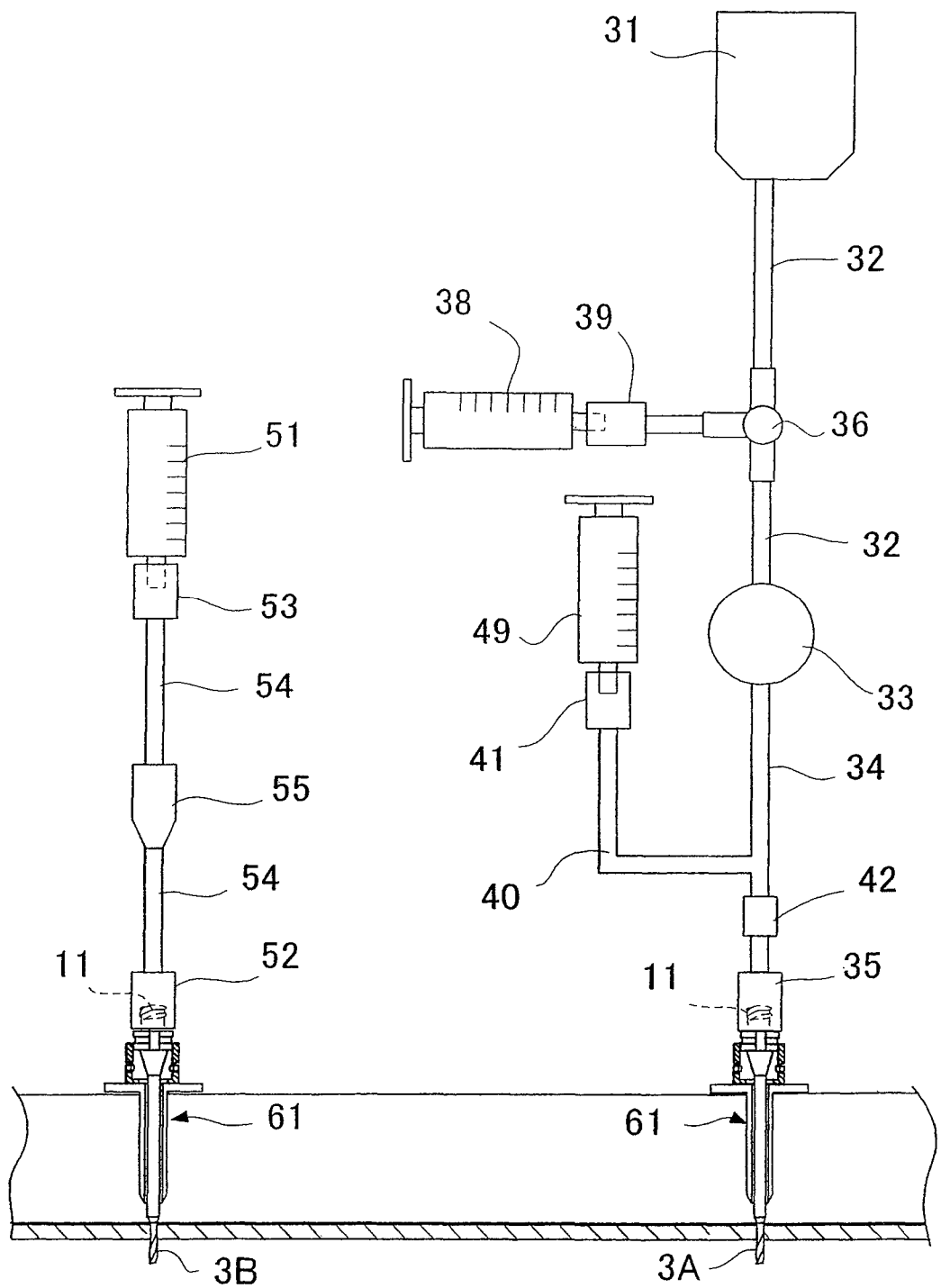
FIG. 15 is an explanatory diagram following FIG. 14 in sequence.

Next, as shown in FIG. 15, the injection orifice of the injection syringe 51, which is filled with a perfusion medium such as physiological saline, is connected to the fifth lure lock connector 53, and the lure lock connector 11 of the tubular mantle 3B for injection is connected to the fourth lure lock connector 52. The first lure lock connector 35 of the harvest circuit is connected to the lure lock connector 11 of the tubular mantle 3A for harvesting bone marrow. The fifth lure lock connector 53 may also be connected to, instead of the syringe 51, a parenteral fluid pump filled with the perfusion medium or a parenteral fluid bag filled with the perfusion medium and hung on a parenteral fluid stand at an appropriate height, neither of which is illustrated.

Next, the perfusion medium is slowly injected into the ilium from the injection syringe 51 (or from a parenteral fluid pump or a parenteral fluid bag positioned at a regulated height, neither of which is illustrated). At the same time, the three-way stopcock 36 of the harvest circuit is switched to the aspiration side of the syringe 38 and an aspiration operation is conducted with the syringe 38. Bone marrow is thereby temporarily aspirated into the syringe 38. The three-way stopcock 36 is then switched to the side to allow discharge from the syringe 38 into the fluid collection bag 31, and the syringe 38 is operated to discharge the bone marrow into the fluid collection bag 31. According to need, heparinized saline solution is injected from a syringe 49 to prevent blood clotting. After the bone marrow is collected in the fluid collection bag 31, a connector (not illustrated) that connects the first tube 32 and the fluid collection bag 31 is detached, and the opening of the fluid collection bag 31 is closed with a sterilized cap, which is not illustrated. The bag is then delivered to a desired place, and, or otherwise immediately after the above operation, the collected bone marrow is centrifuged to collect bone marrow cell fractions. Such an integrated process using the bone marrow harvesting set can minimize the exposure of harvested bone marrow to a non-aseptic environment.

The invention claimed is:

1. A bone marrow harvesting drill comprising:
   an inner needle having a cutting edge and a shank at a tip and a rear end thereof, respectively;
   a tubular mantle that receives the inner needle thereinto so that the inner needle and the tubular mantle are detachably attached in such a manner that the tip and the rear end of the inner needle project from the tubular mantle; and
   a lock mechanism that prevents the axial rotation of the tubular mantle and the inner needle relative to each other;
   the inner needle having a groove formed at the tip thereof projecting from the tubular mantle when the inner needle is inserted into the tubular mantle for discharging bone scraps produced by the cutting edge at the tip of the inner needle;
   the tubular mantle having a cutting edge formed at a tip edge thereof and a helical groove extending from the tip edge of the tubular mantle to at least part of a peripheral surface of the tubular mantle so as to be flush with the groove of the inner needle, the helical groove having a depth that is less than a thickness of the tubular mantle; and
   at least part of a leading edge of the helical groove being formed as a concave notch.

2. A bone marrow harvesting drill according to claim 1, wherein the cutting edge of the tubular mantle is formed so as to be flush with the cutting edge of the inner needle.

3. A bone marrow harvesting drill according to claim 1, wherein the tubular mantle has a flank at the tip edge thereof, the flank being formed so as to be flush with a flank formed at the tip of the inner needle.

4. A bone marrow harvesting drill according to claim 1, wherein the tubular mantle has a lure lock connector formed at a rear end thereof.

5. A bone marrow harvesting drill according to claim 4, further comprising a cap for sealing the lure lock connector that is formed at the rear end of the tubular mantle, the cap being attached to the inner needle.

6. A bone marrow harvesting drill according to claim 5, wherein the lock mechanism comprises:
   a locking part formed on the cap; and
   a lock-receiving part formed in the tubular mantle for engaging with the locking part;
   the lock mechanism being structured so that the engagement of the locking part with the lock-receiving part prevents the axial rotation of the inner needle relative to the tubular mantle.

7. A bone marrow harvesting drill according to claim 1, wherein the helical groove extends along an outer peripheral surface of the tubular mantle.

8. A bone marrow harvesting drill comprising:

an inner needle having a cutting edge and a shank at a tip and a rear end thereof, respectively;

a tubular mantle that receives the inner needle thereinto so that the inner needle and the tubular mantle are detachably attached in such a manner that the tip and the rear end of the inner needle project from the tubular mantle; and a lock mechanism that prevents the axial rotation of the tubular mantle and the inner needle relative to each other;

the inner needle having a groove formed at the tip thereof projecting from the tubular mantle when the inner needle is inserted into the tubular mantle for discharging bone scraps produced by the cutting edge at the tip of the inner needle;

the tubular mantle having a cutting edge formed at a tip edge thereof and a helical groove extending from the tip edge of the tubular mantle to at least part of a peripheral surface of the tubular mantle so as to be flush with the groove of the inner needle; and at least part of a leading edge of the helical groove being formed as a concave notch, wherein the helical groove does not extend through a thickness of the tubular mantle.

* * * * *